United States Patent
Broell et al.

(10) Patent No.: US 8,337,671 B2
(45) Date of Patent: Dec. 25, 2012

(54) METHOD FOR PURIFYING POLYMERIZABLE COMPOUNDS

(75) Inventors: Dirk Broell, Langen (DE); Hermann Siegert, Seeheim-Jugenheit (DE)

(73) Assignee: Evonik Röhm GmbH, Darmstadt (DE)

( * ) Notice: Subject to any disclaimer, the term of this patent is extended or adjusted under 35 U.S.C. 154(b) by 670 days.

(21) Appl. No.: 12/300,189

(22) PCT Filed: Mar. 14, 2007

(86) PCT No.: PCT/EP2007/052397
§ 371 (c)(1),
(2), (4) Date: Nov. 10, 2008

(87) PCT Pub. No.: WO2007/147651
PCT Pub. Date: Dec. 27, 2007

(65) Prior Publication Data
US 2009/0166176 A1    Jul. 2, 2009

(30) Foreign Application Priority Data
Jun. 23, 2006    (DE) .................. 10 2006 029 319

(51) Int. Cl.
*B01D 3/34*    (2006.01)
*C07C 51/44*    (2006.01)
*C07C 57/07*    (2006.01)

(52) U.S. Cl. .............. 203/8; 203/9; 203/58; 203/65; 203/69; 203/70; 203/98; 203/DIG. 21; 562/600

(58) Field of Classification Search .............. 203/8, 9, 203/57, 58, 65, 69, 70, 98, DIG. 21; 560/218; 562/600
See application file for complete search history.

(56) References Cited

U.S. PATENT DOCUMENTS

| | | | |
|---|---|---|---|
| 4,608,127 A * | 8/1986 | Sakuma et al. .............. 203/48 |
| 5,154,800 A | 10/1992 | Berg |
| 6,649,787 B1 * | 11/2003 | Nakahara et al. ............. 560/205 |
| 6,743,407 B2 | 6/2004 | Schaefer et al. |
| 6,977,310 B2 | 12/2005 | Ackermann et al. |
| 6,979,432 B2 | 12/2005 | Schaefer et al. |
| 7,288,402 B2 | 10/2007 | Osswald et al. |
| 7,491,521 B2 | 2/2009 | Osswald et al. |
| 7,714,165 B2 * | 5/2010 | Broell et al. .................. 562/892 |
| 2005/0077240 A1 | 4/2005 | Hofer et al. |
| 2006/0151309 A1 | 7/2006 | Schroder |
| 2006/0211880 A1 | 9/2006 | Ackerman et al. |
| 2008/0194862 A1 | 8/2008 | Ackermann et al. |
| 2008/0194875 A1 | 8/2008 | Ackermann et al. |

(Continued)

FOREIGN PATENT DOCUMENTS
DE    102 56 147    12/2003
(Continued)

OTHER PUBLICATIONS

U.S. Appl. No. 12/298,034, filed Oct. 22, 2008, May, et al.
(Continued)

*Primary Examiner* — Virginia Manoharan
(74) *Attorney, Agent, or Firm* — Oblon, Spivak, McClelland, Maier & Neustadt, L.L.P.

(57) ABSTRACT

Process for distillatively purifying polymerizable compounds using a high-boiling, inert, thermally long-term-stable substance as a boiling oil, characterized in that the boiling oil is disposed in the bottom of a rectification column.

17 Claims, 1 Drawing Sheet

U.S. PATENT DOCUMENTS

| | | |
|---|---|---|
| 2008/0248538 A1 | 10/2008 | Osswald et al. |
| 2008/0269431 A1 | 10/2008 | Sarcinelli et al. |
| 2009/0118533 A1 | 5/2009 | Broell et al. |

FOREIGN PATENT DOCUMENTS

| | | |
|---|---|---|
| EP | 0 188 775 | 7/1986 |
| WO | 2005/035478 A2 | 4/2005 |

OTHER PUBLICATIONS

U.S. Appl. No. 12/299,217, filed Oct. 31, 2008, Broell, et al.
U.S. Appl. No. 12/307,773, filed Jan. 7, 2009, Ackermann, et al.
U.S. Appl. No. 12/441,145, filed Mar. 13, 2009, May, et al.
U.S. Appl. No. 12/515,036, filed May 15, 2009, May et al.
U.S. Appl. No. 12/443,784, filed Mar. 31, 2009, Vogel, et al.
U.S. Appl. No. 12/442,415, filed Mar. 23, 2009, Vogel, et al.
U.S. Appl. No. 12/303,161, filed Dec. 2, 2008, Marx, et al.
U.S. Appl. No. 12/517,563, filed Jun. 4, 2009, Broell.
Chinese Office Action issued in CN 200780020824.3, dated Dec. 5, 2011.

* cited by examiner

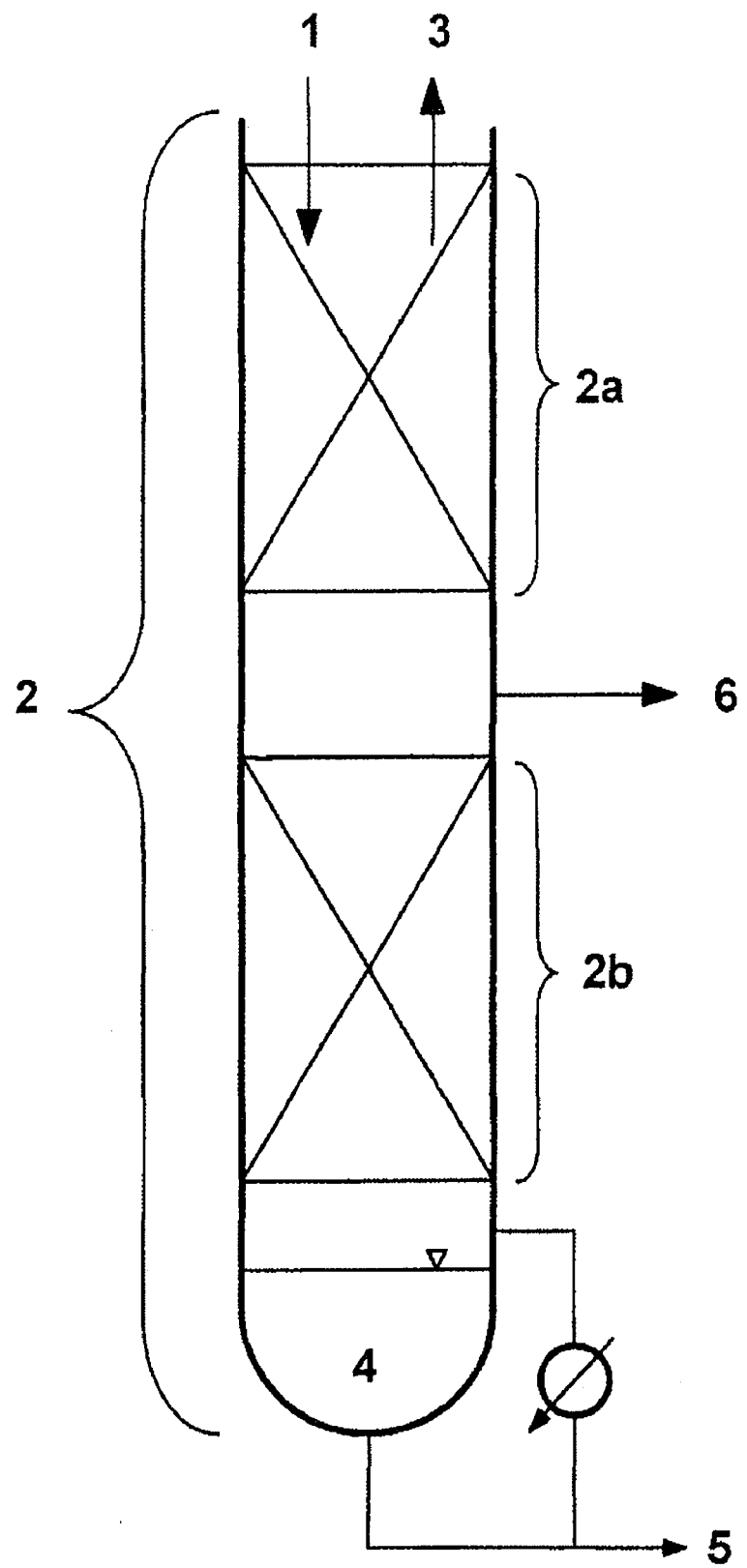

METHOD FOR PURIFYING POLYMERIZABLE COMPOUNDS

CROSS-REFERENCE TO RELATED APPLICATIONS

The present application is a National Stage (371) of PCT/EP07/52397, filed on Mar. 14, 2007, which claims priority to DE 10 2006 029 319.3, filed Jun. 23, 2006.

The invention describes a process for distillatively purifying polymerizable compounds and the use of a boiling oil for the distillative purification of polymerizable compounds.

DE-A-2136396 describes a process for obtaining anhydrous acrylic acid by countercurrent scrubbing of the reaction gases in an absorber column with a high-boiling, inert, extremely hydrophobic solvent. Suitable solvents are hydrocarbons of the middle oil fraction, heat carrier oils with boiling points above 170° C. (at standard pressure) or diphenyl ether, diphenyl and/or mixtures thereof. The solvent is fed in via the top of the column. For the absorption, a minimum temperature of 30-80° C. at standard pressure is established.

EP-A-188775 discloses a process for obtaining anhydrous methacrylic acid, in which the reaction gases obtained are scrubbed with an inert, high-boiling, hydrophobic, organic solvent, especially by countercurrent scrubbing in an absorber column. The solvent, such as diphenyl, diphenyl ether, dibenzofuran and/or mixtures thereof, is added via the top of the column. The absorption temperature is 40-120° C. at standard pressure.

A disadvantage of the aforementioned processes is that, to obtain anhydrous acrylic acid or methacrylic acid, further desorption and distillation steps have to follow in order to remove the target product from the solvent used again.

It is an object of the present invention to provide a process for distillatively purifying polymerizable compounds, in which the substances used as assistants can be recycled into the plant without further purification, and not more than 10% of the assistant, based on the target product, is discharged. In addition, the process shall ensure in particular that polymerization of the target product is avoided. The object is achieved by performing the distillative purification of the polymerizable compound in the presence of a high-boiling, inert, thermally long-term-stable substance, this substance referred to as a boiling oil being present in the bottom of a rectification column. This rules out long residence times of the polymerization-prone target product in the bottom, since the concentration of the polymerization-prone compound decreases greatly as a result of the heat exchange with the boiling oil vapours in the direction of the bottom and hence in the direction of increasing temperature, which largely averts the risk of polymerization.

The invention therefore provides a process for distillatively purifying polymerizable compounds using a high-boiling, inert, thermally long-term-stable substance as a boiling oil, characterized in that the boiling oil is disposed in the bottom of a rectification column.

For the process according to the invention, the boiling oil used is a high-boiling, inert, thermally long-term-stable substance having a boiling point higher than the boiling point of the pure target product, in order to ensure its distillative removal. The boiling point of the boiling oil should, though, not be too high either, in order to reduce the thermal stress on the pure polymerizable compound.

In general, the boiling point of the boiling oil at standard pressure (1013 mbar) is 150 to 400° C., in particular 200 to 300° C.

Suitable boiling oils include relatively long-chain unbranched paraffins having 12-20 carbon atoms, aromatic compounds such as Diphyl (eutectic mixture of 75% biphenyl oxide and 25% biphenyl), alkyl-substituted phenols or naphthalene compounds, sulpholane (tetrahydrothiophene 1,1-dioxide) or mixtures thereof.

Suitable examples are the boiling oils shown below:

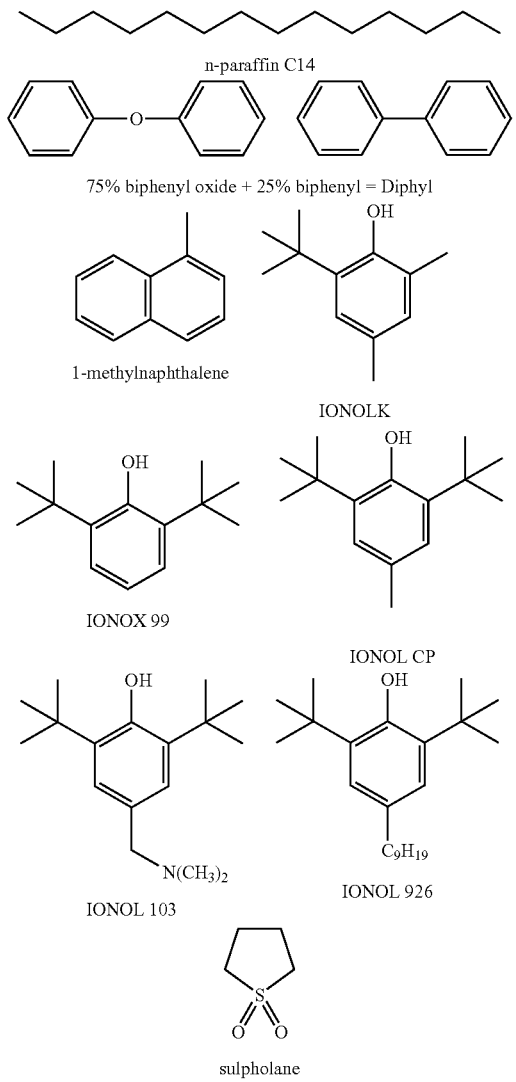

Particular preference is given to using 2,6-di-tert-butyl-para-cresol, 2,6-di-tert-butylphenol, sulpholane, Diphyl or mixtures thereof, very particular preference to using sulpholane.

For the process according to the invention, any rectification column which has preferably 5 to 50 separating stages can be used. In the present invention, the number of separating stages refers to the number of trays in a tray column multiplied by the tray efficiency, or the number of theoretical plates in the case of a column with structure packing or a column with random packing.

Examples of a rectification column with trays include those such as bubble-cap trays, sieve trays, tunnel-cap trays, valve trays, slot trays, slotted sieve trays, slotted bubble-cap trays, jet trays, centrifugal trays; examples of a rectification column with random packings include those such as Raschig rings, Lessing rings, Pall rings, Berl saddles, Intalox saddles; and examples of a rectification column with structured packings include those of the Mellapak (Sulzer), Rombopak (Kühni), Montz-Pak (Montz) types, and structured packings with catalyst pockets, for example Katapak (Sulzer).

A rectification column with combinations of regions of trays, of regions of random packings and/or of regions of structured packings may likewise be used.

Preference is given to using a rectification column with random packings and/or structured packings. The rectification column can be produced from any material suitable therefor. These include stainless steel and inert materials.

The rectification column is preferably operated under reduced pressure at an absolute pressure of 1 to 500 mbar, preferably at an absolute pressure of 1 to 100 mbar. The temperature in the bottom of the rectification column is determined by the boiling oil used and the system pressure which exists.

Polymerizable compounds are generally understood to mean monomers with at least one reactive double bond or other reactive functional groups. They include compounds having carbon-carbon multiple bonds (olefins, alkynes, vinyl, (meth)acryloyl compounds), cyclic ethers, esters or amides (oxiranes, lactones, lactams), unsaturated cyclic hydrocarbons, and also those with isocyanate or H-acidic amino, hydroxyl or carboxyl groups. Suitable polymerizable compounds are known to those skilled in the art from the literature, for example from J. Brandrup, E. H. Immergut and E. A. Grulke, Polymer Handbook, 4th ed., Hoboken, John Wiley and Sons, 1999, pages III-1 to III-41, which is explicitly incorporated by reference.

The polymerizable compound to be purified is fed in preferably above the middle region of the column. Low-boiling impurities are drawn off at the top of the column; high-boiling impurities are discharged from the column bottom. The pure target product is preferably discharged at a side draw below the middle region of the column.

The column may also be connected to other apparatus, for example further apparatus for substance separation and/or a reactor. A reaction region may also be arranged within the column. The column may also be divided into a plurality of separating segments which fulfil different tasks.

In order to avoid undesired polymerizations of the polymerizable compound to be purified, a polymerization inhibitor is optionally added. The polymerization inhibitors usable with preference include octadecyl 3-(3,5-di-tert-butyl-4-hydroxyphenyl)propionate, phenothiazine, hydroquinone, hydroquinone monomethyl ether, 4-hydroxy-2,2,6,6-tetramethylpiperidinooxyl (TEMPOL), 2,4-dimethyl-6-tert-butylphenol, 2,6-di-tert-butylphenol, 2,6-di-tert-butyl-4-methylphenol, para-substituted phenylenediamines, for example N,N'-diphenyl-p-phenylenediamine, 1,4-benzoquinone, 2,6-di-tert-butyl-alpha-(dimethylamino)-p-cresol, 2,5-di-tert-butylhydroquinone or mixtures of two or more of these stabilizers.

The inhibitor is metered in preferably at the top of the column. From the column bottom, high boilers such as added inhibitors can be discharged by customary methods, for example by means of a thin-film evaporator or an apparatus which performs similar tasks, which recycles evaporating substances into the rectification column and discharges non-evaporating high boilers.

The invention further provides for the use of the above-mentioned high-boiling, inert, thermally long-term-stable substance as a boiling oil in the bottom of a rectification column for the distillative purification of polymerizable compounds.

The process according to the invention enables the polymerizable compound to be obtained without losses by undesired polymerization in high purity by simple removal, and the boiling oil used can be recycled into the plant without further purification.

BRIEF DESCRIPTION OF THE DRAWING

One embodiment of the process according to the invention is shown schematically in FIG. 1.

The monomer to be purified=crude monomer (1) passes into the lower section of a rectification column (2). Here, the removal of components which have a lower boiling point (3) than the monomer to be purified takes place in the separating region (2*a*). In the separating region (2*b*) of the column, the monomer is separated from the boiling oil (4) present in the bottom and from components which have a higher boiling point than the monomer to be purified. High boilers present in the bottom can be discharged by customary methods (5), for example by means of a thin-film evaporator or an apparatus which performs similar tasks, which recycles evaporating substances into the rectification column and discharges non-evaporating high boilers. The highly pure monomer (6) is drawn off, preferably in gaseous form, between separating region (2*a*) and (2*b*).

The examples which follow illustrate the process according to the invention without restricting it.

EXAMPLE 1

Purification of Methacrylic Anhydride

The purification of methacrylic anhydride was performed in the lower section of a rectification column according to FIG. 1.

The rectification column had twelve separating stages in the separating region (2*a*) and eight separating stages in the separating region (2*b*). This column had an internal diameter of 100 mm and was equipped with Sulzer CY structured packings (separating region 2*a*) and Montz BSH 400 structured packings (separating region 2*b*). The pressure in the column bottom was 35 mbar. Under steady-state conditions, a temperature profile of 164° C. (bottom) to 66° C. (upper end of the separating region 2*a*) was established. The discharge of methacrylic anhydride at the side draw (between separating region 2*a* and 2*b*) and the heating steam output of the bottom evaporator were effected under temperature control in the particular regions.

In the bottom of the rectification column, 6 kg of sulpholane were used as the boiling oil (4). The evaporator used was a falling-film evaporator.

At the side draw, methacrylic anhydride was withdrawn with a purity of 99.7% (GC analysis).

EXAMPLE 2

Purification of Acrylic Anhydride

The purification of acrylic anhydride was performed as explained in Example 1 in the same lower section of a rectification column according to FIG. 1. The pressure in the column bottom was 35 mbar. Under steady-state conditions, a temperature profile of 164° C. (bottom) to 54° C. (upper end of the separating region 2*a*) was established. The discharge of acrylic anhydride at the side draw (between separating region 2a and 2b) and the heating steam output of the bottom evaporator were effected under temperature control in the particular regions.

In the bottom of the rectification column, 6 kg of sulpholane were used as boiling oil (4). The evaporator used was a falling-film evaporator.

At the side draw, acrylic anhydride was withdrawn with a purity of 99.7% (GC analysis).

The invention claimed is:

1. A process for distillatively purifying polymerizable compounds comprising distillatively processing a crude monomer wherein a boiling oil having a boiling point at 1013 mbar of 150 to 400° C. disposed in the bottom of a rectification column and not more than 10% of boiling oil, based on the polymerizable compounds, are discharged, wherein the boiling oil remains in the bottom of said rectification column and can be recycled without further purification.

2. The process according to claim 1, wherein the boiling point of the boiling oil at 1013 mbar is 200 to 300° C.

3. The process according to claim 1, wherein the boiling oil is at least one selected from the group consisting of an unbranched paraffin having 12-20 carbon atoms, an aromatic compound, and an alkyl-substituted phenol.

4. The process according to claim 3, wherein said boiling oil is an aromatic compound and said aromatic compound is Diphyl.

5. The process according to claim 1, wherein the boiling oil is at least one selected from the group consisting of 2,6-di-tert-butyl-para-cresol, 2,6-di-tert-butylphenol, sulpholane, and Diphyl.

6. The process according to claim 1, wherein the boiling oil is sulpholane.

7. The process according to claim 1, wherein the boiling oil is at least one selected from the group consisting of a naphthalene compound and a sulpholane.

8. A process for distillatively purifying polymerizable compounds, comprising:

passing a crude monomer into a lower section of a rectification column that comprises a boiling oil and not more than 10% of boiling oil, based on the polymerizable compounds, are discharged;

separating said crude monomer from said boiling oil to obtain a polymerizable compound; and withdrawing said polymerizable compound from said rectification column, wherein the boiling oil remains in the bottom of said rectification column and can be recycled without further purification.

9. The process according to claim 8, wherein said boiling oil exhibits a boiling point ranging from 150 to 400° C. at 1013 mbar.

10. The process according to claim 8, wherein said boiling oil exhibits a boiling point ranging from 200 to 300° C. at 1013 mbar.

11. The process according to claim 8, wherein said boiling oil is at least one selected from the group consisting of an unbranched paraffin having 12-20 carbon atoms and an alkyl-substituted phenol.

12. The process according to claim 8, wherein said boiling oil is Diphyl, wherein said Diphyl is a mixture of 75% biphenyl oxide and 25% biphenyl.

13. The process according to claim 8, wherein said boiling oil is at least one selected from the group consisting of 2,6-di-tert-butyl-para-cresol, 2,6-di-tert-butylphenol, sulpholane, and Diphyl.

14. The process according to claim 8, wherein said boiling oil is sulpholane.

15. The process according to claim 8, wherein said crude monomer is methacrylic anhydride or acrylic anhydride.

16. The process according to claim 8, wherein a yield of said separated monomer is 99.7%.

17. The process according to claim 8, wherein said boiling oil is at least one selected from the group consisting of Diphyl, an alkyl-substituted naphthalene compound, and sulpholane.

* * * * *